United States Patent
Sato

(10) Patent No.: US 10,870,108 B2
(45) Date of Patent: Dec. 22, 2020

(54) LIQUID ACCOMMODATING CONTAINER

(71) Applicant: ARKRAY, Inc., Kyoto (JP)

(72) Inventor: Yoshiharu Sato, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 246 days.

(21) Appl. No.: 16/025,154

(22) Filed: Jul. 2, 2018

(65) Prior Publication Data

US 2019/0009269 A1 Jan. 10, 2019

(30) Foreign Application Priority Data

Jul. 4, 2017 (JP) .................................. 2017-131209

(51) Int. Cl.
*B65D 75/32* (2006.01)
*B65D 83/04* (2006.01)
*B65D 1/32* (2006.01)
*A61M 35/00* (2006.01)
*A61J 1/00* (2006.01)
*A61J 1/20* (2006.01)
*B01L 3/00* (2006.01)

(52) U.S. Cl.
CPC ................. *B01L 3/502* (2013.01); *A61J 1/00* (2013.01); *A61M 35/003* (2013.01); *B65D 75/327* (2013.01); *B65D 83/04* (2013.01); *B01L 2200/16* (2013.01); *B01L 2300/044* (2013.01); *B01L 2300/0672* (2013.01); *B01L 2300/123* (2013.01); *B01L 2300/161* (2013.01)

(58) Field of Classification Search
None
See application file for complete search history.

(56) References Cited

U.S. PATENT DOCUMENTS

| | | | | |
|---|---|---|---|---|
| 6,036,016 A | * | 3/2000 | Arnold | B65D 75/327 206/469 |
| 2004/0247628 A1 | * | 12/2004 | Lintz | A61K 9/08 424/400 |
| 2008/0283439 A1 | * | 11/2008 | Sullivan | A61M 15/0061 206/531 |
| 2013/0327672 A1 | * | 12/2013 | Kurowski | B01L 3/52 206/462 |
| 2017/0291747 A1 | * | 10/2017 | Janta | B81C 1/00158 |

* cited by examiner

*Primary Examiner* — Neil N Turk
(74) *Attorney, Agent, or Firm* — Studebaker & Brackett PC

(57) ABSTRACT

A liquid accommodating container includes an accommodating portion configured to accommodate, in a hermetically closed state, a liquid for testing a measuring apparatus, a storage portion configured to store the liquid, and a coupling portion configured to couple the accommodating portion and the storage portion in a state that one of the accommodating portion and the storage portion is foldable back to the other.

8 Claims, 5 Drawing Sheets

LIQUID ACCOMMODATING CONTAINER

CROSS-REFERENCE TO RELATED APPLICATION

This application claims the benefit of Japanese Patent Application No. 2017-131209 filed on Jul. 4, 2017 in the Japanese Patent Office, the disclosure of which is herein incorporated in its entirety by reference.

FIELD

The present disclosure relates to a liquid accommodating container.

BACKGROUND

A glucose measuring system is known as an example of the body fluid measuring system. The glucose measuring system includes a measuring apparatus coupled with a disposable type glucose sensor to measure the glucose concentration in blood spotted onto the glucose sensor so that an obtained result is displayed.

A test, which is based on the use of a liquid referred to as "control solution", is carried out in order to maintain the measurement accuracy brought about by the measuring apparatus. In the test, the control solution is spotted onto the glucose sensor to perform the measurement by means of the measuring apparatus, and it is judged that the measuring apparatus is normal if the numerical value of a measurement result is included in a predetermined range.

The test, which is based on the use of the control solution as described above, has been carried out in the institution other than home, including, for example the medical institution and the inspection institution. The control solution is accommodated in a bottle having a screw cap. An amount of the control solution, which is required for performing the test once, is dripped from the bottle, and the control solution is spotted onto a glucose sensor as a test object.

SUMMARY

In recent years, the cases, in which the measurement of the glucose concentration is performed at home, are progressively increased. The cases, in which the test based on the use of the control solution is also performed at home, are anticipated to increase. The frequency to perform the test at home is considered to be lower than the frequency to perform the test in the medical institution and the inspection institution as described above.

Therefore, if the bottle as described above is applied to the test at home as it is, the control solution is consequently provided in an amount which is not less than the necessary amount. It is feared that such application may disturb the reduction of the cost. It is also conceived that an amount of the control solution, which is provided while considering the frequency of the test performed at home, is accommodated in the bottle as described above.

However, it is not affirmed that the provision of the control solution with the bottle as described above is preferred, if consideration is made about the problem of the storage performance of the bottle, the complication of the storage of the uncapped bottle, and the deterioration of the control solution caused by the uncapping. Further, such a case is also assumed that a user of the measuring apparatus may feel any inconvenience when the screw cap is opened/closed.

The problems as described above are not limited to only the accommodating container for accommodating the control solution, and the problems generally hold for the liquid accommodating container for testing the measuring apparatus in which the frequency of use is not so large.

One of embodiments is a liquid accommodating container. The liquid accommodating container includes:

an accommodating portion configured to accommodate, in a hermetically closed state, a liquid for testing a measuring apparatus;

a storage portion configured to store the liquid; and a coupling portion configured to couple the accommodating portion and the storage portion in a state that one of the accommodating portion and the storage portion is foldable back to the other.

The object and advantages of the invention will be realized and attained by means of the elements and combinations particularly pointed out in the claims.

It is to be understood that both the foregoing general description and the following detailed description are exemplary and explanatory and are not restrictive of the invention.

DESCRIPTION OF EMBODIMENTS

An explanation will be made below with reference to the drawings about a liquid accommodating container according to embodiments. The structure or arrangement of the embodiments explained below is described by way of example, and the embodiments are not limited to the structure or arrangement.

First Embodiment

Figure 1:
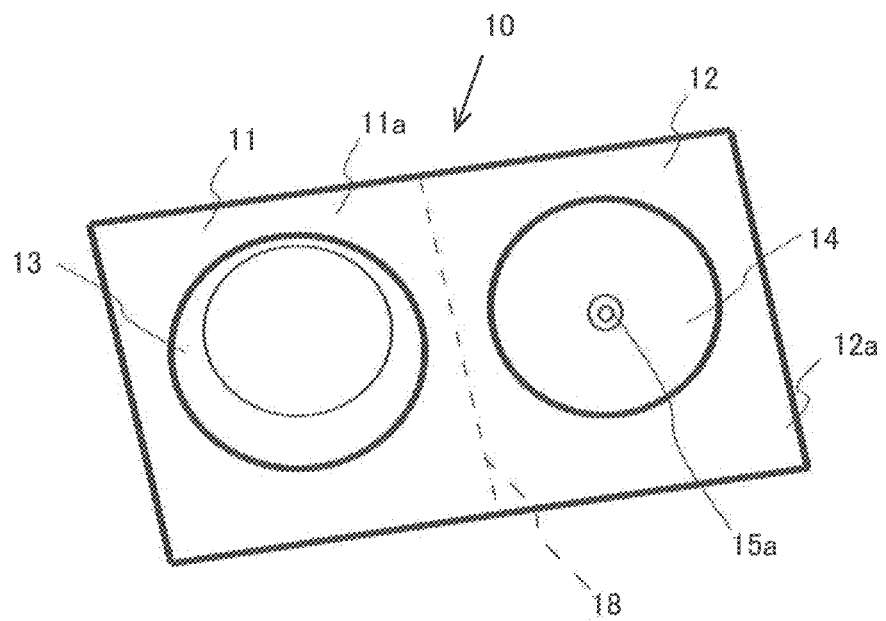
FIG. 1 illustrates a front surface of an accommodating container according to a first embodiment.
Figure 2:
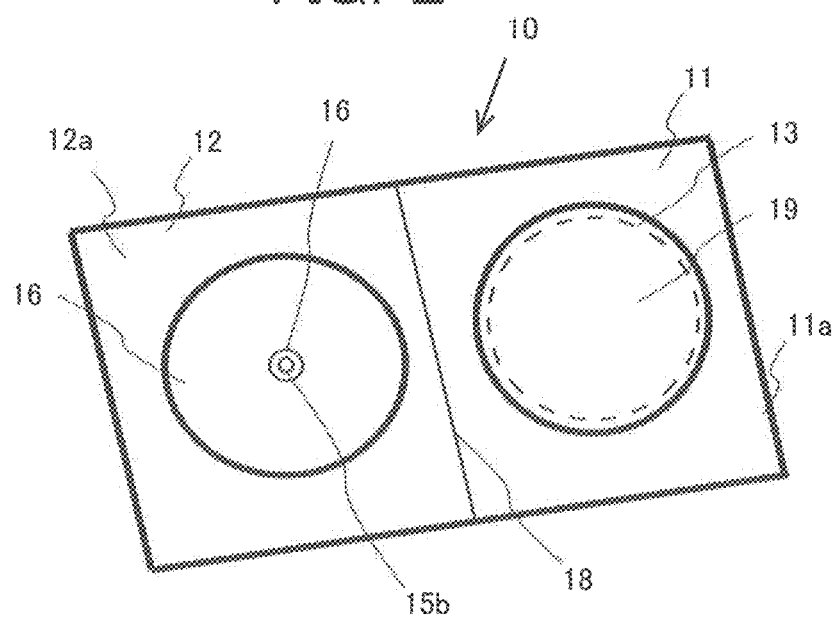
FIG. 2 illustrates a back surface of the accommodating container according to the first embodiment.
Figure 3:
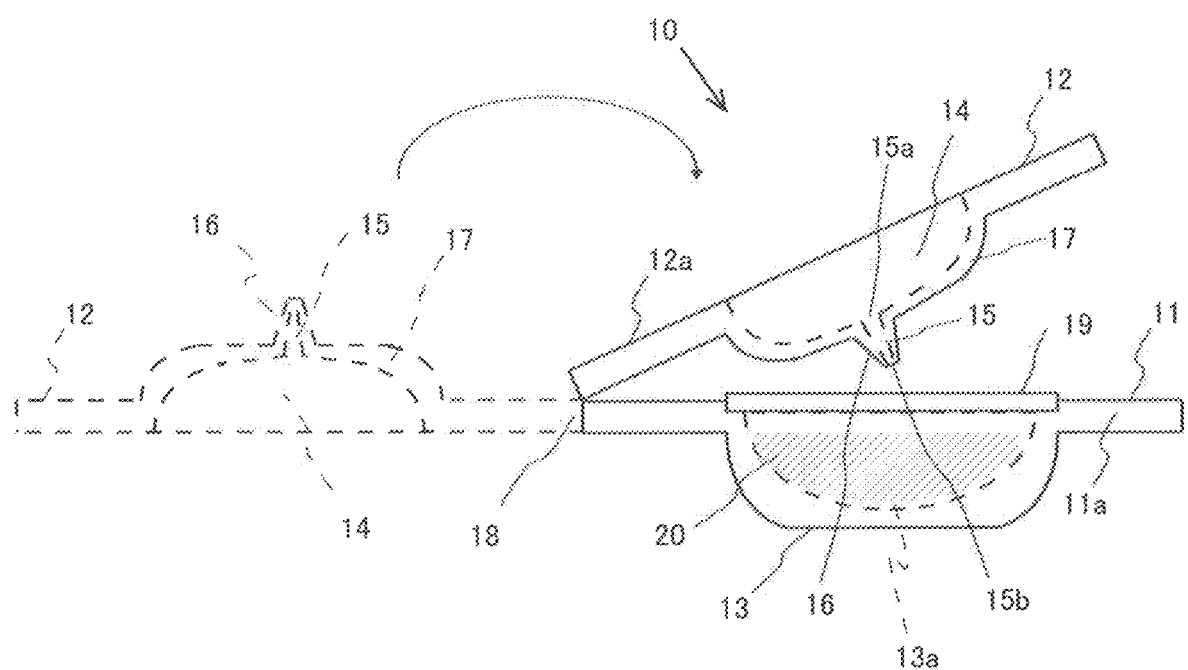
FIG. 3 schematically illustrates a fold-back state of the accommodating container according to the first embodiment.
Figure 4:
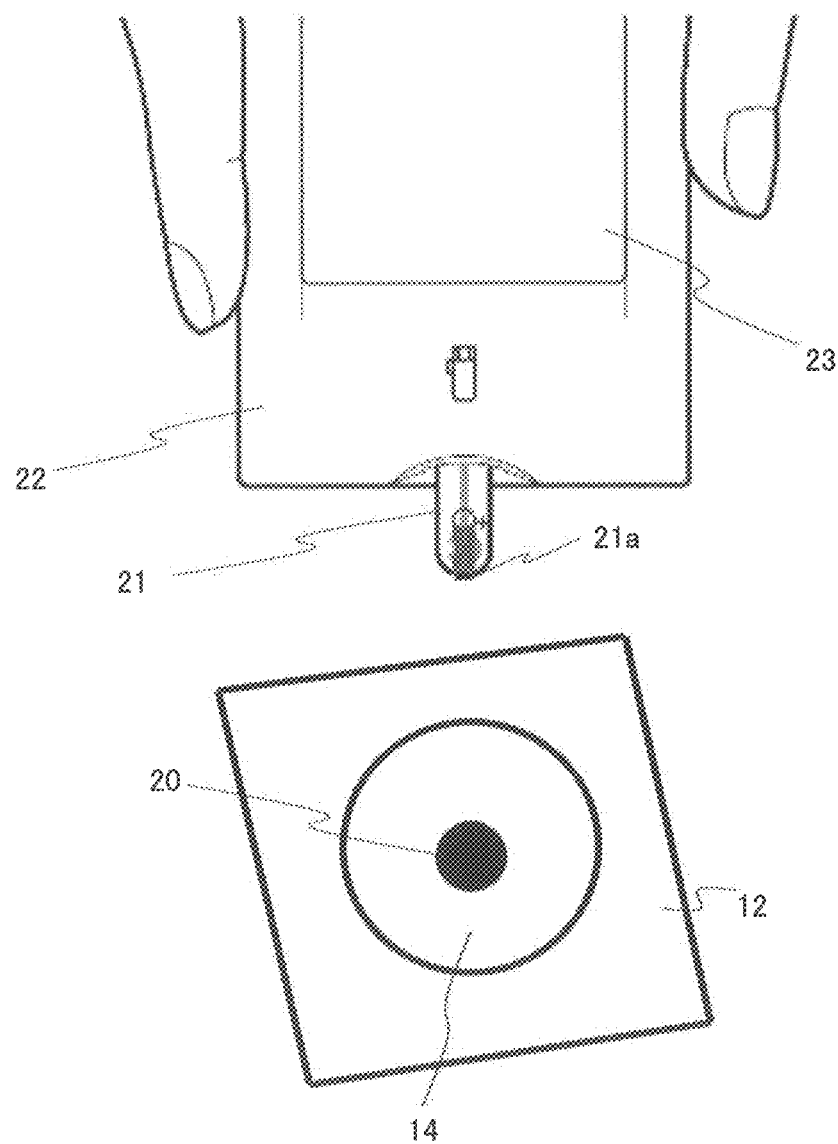
FIG. 4 illustrates a state of use of the accommodating container according to the first embodiment.

FIG. 1 illustrates a front surface of an accommodating container according to a first embodiment. FIG. 2 illustrates a back surface of the accommodating container according to the first embodiment. FIG. 3 schematically illustrates a fold-back state of the accommodating container according to the first embodiment. Further, FIG. 4 illustrates a state of use of the accommodating container according to the first embodiment.

The accommodating container 10 is an accommodating container for accommodating a control solution to be applied to the test for a glucose measuring system or a measuring apparatus for measuring the glucose concentration in a sample (e.g., blood, interstitial fluid, etc.) as an example of the body fluid measuring system. However, the body fluid may be one other than blood.

The accommodating container 10 comprises a first member 11 which includes an accommodating portion 13, a second member 12 which includes a storage portion 17, and a coupling portion which couples the second member 12 (the storage portion 17) and the first member 11 (the accommodating portion 13) so that the second member 12 (the storage portion 17) is foldable back to the first member 11 (the accommodating portion 13). The first member and the second member are made of resin (plastic) and the like.

In the example illustrated in FIGS. 1 to 3, the first member 11 includes the accommodating portion 13 which accommodates, in a hermetically closed state, a control solution 20 (FIG. 3) as an example of the liquid for testing the measuring apparatus. The second member 12 includes the storage portion 17. The storage portion 17 is coupled to the accommodating portion 13 so that the storage portion 17 is foldable back to the accommodating portion 13. The first member 11 includes the circular bowl-shaped accommodating portion 13 having a recess 13a which is open on the back surface of the accommodating container 10, and a flange 11a which is coupled to the edge portion of the accommodating portion 13.

The recess 13a is filled with the control solution 20. The recess 13a, which accommodates the control solution 20, is hermetically closed by a lid 19. The amount of the control solution retained in the recess 13a is, for example, 100 to 200 microliters. However, the substantial amount of use the control solution is smaller than the accommodated amount. The lid 19 is, for example, a film made of resin (plastic) and/or aluminium. The lid 19 is provided by using an appropriate technique including, for example, the adhesion with an adhesive, the fusion with heat, and the pressure joining. In this way, the accommodating portion 13 of the first member 11 accommodates the control solution 20 in the hermetically closed state.

The second member 12 includes a recess 14 which is open on the front surface (FIG. 1) of the accommodating container 10, a flange 12a which is coupled to the edge portion of the recess 14, a storage portion 17 which protrudes to the back surface side of the accommodating container 10 as a result of the formation of the recess 14, and a projection portion 16 which projects from a central portion of the storage portion 17. The projection portion 16 projects in the fold-back direction (see the arrow illustrated in FIG. 3) in which the second member 12 is folded back with respect to the accommodating portion 13.

The interior of the projection portion 16 is hollow, and both ends of the projection portion 16 are open. That is, one end of the projection portion 16 has an opening 15a which is coupled to the storage portion 17 and which makes communication between the bottom of the recess 14 and the interior of the projection portion 16. The other end of the projection 16 is formed with a through-hole 15 which has an opening 15b and which penetrates from the bottom of the recess 14 to the other end of the projection portion 16. In this way, the storage portion 17 is formed to have a funnel-shaped form.

The flange 11a and the flange 12a function as the coupling portions for coupling the accommodating portion 13 and the storage portion 17. The flange 11a and the flange 12a are formed to have rectangular shapes respectively, and respective sides thereof are coupled on an identical plane. When the front surface of the accommodating container 10 is arranged while being directed upwardly, then the accommodating portion 13 is arranged at an upward position of the accommodating container 10, and the storage portion 17 is arranged at a downward position of the accommodating container (see FIG. 3).

In the embodiment, the first member 11 including the accommodating portion 13 and the second member 12 including the storage portion 17 are integrally molded by using, for example, a resin. A groove 18 is formed between the first member 11 and the second member 12 on the back surface of the accommodating container 10 (FIG. 2). The groove 18 comparts the flange 11a and the flange 12a to form the boundary portion (corresponding to a coupling portion) between the first member 11 (corresponding to an accommodating portion) and the second member 12 (corresponding to a storage portion). The groove 18 is a cut or notch formed, for example, by the half-cut processing. A perforation or a crease may be provided in place of the groove 18. At least one of the groove, the perforation, and the crease may be formed.

Owing to the groove 18, as illustrated in FIG. 3, the second member 12 (the storage portion 17) can be folded back to the first member 11 (the accommodating portion 13) in the state in which the back surface of the accommodating container 10 is directed upwardly. As a result of the folding back, the forward end of the projection portion 16 abuts against the lid 19. The forward end of the projection portion 16 breaks (perforates) the lid 19, and the forward end of the projection portion 16 is inserted into the control solution 20 retained in the recess 13a.

Accordingly, the control solution 20 is sucked through the opening 15b in accordance with the capillary phenomenon. The control solution 20 passes through the through-hole 15, the control solution 20 is discharged from the opening 15a, and the control solution is stored in the recess (see FIG. 4). The through-hole 15 functions as the flow passage for the control solution 20 for making communication between the accommodating portion 13 and the storage portion 17. The opening 15a functions as the discharge port for the control solution 20 moved from the accommodating portion 13 to the storage portion 17. However, it is also allowable that control solution 20 contained in the recess 13a passes through the through-hole 15 to move to the recess 14, irrelevant to the capillary phenomenon.

The surface, which forms the recess 14, is, for example, a spherical surface so that the control solution 20 is collected with ease. Alternatively, when the bottom of the recess 14 is formed by a flat surface, and the opening 15a is disposed on the flat surface, then the hydrophobicity of a first area of the flat surface to surround the opening 15a may be lower than the hydrophobicity of a second area to surround the first area. In this case, the control solution 20, which is discharged from the opening 15a and which is dripped to the first area, is limited from being diffused to the second area. Owing to the regulation of the diffusion range as described above, it is possible to provide such a situation that the control solution 20 has a bulged shape (for example, a semispherical shape) which is suitable for the spotting. The first area and the second area function as the limiting portion. Further, the surface, which forms the recess 14, may be formed to have the hydrophobicity.

Note that the following arrangement is also available. That is, when the storage portion 17 is folded back by approximately 180° to the accommodating portion 13, then the storage portion 17 is accommodated in the recess 13a, and the accommodating container 10 is in a state of being folded into two halves. Alternatively, the following arrangement is also available. That is, the folded back storage portion 17 is fitted to the recess 13a to maintain a state of being folded into two halves.

In the embodiment, as illustrated in FIG. 4, the glucose concentration measuring system has a glucose sensor 21 and a measuring apparatus 22 to which the glucose sensor 21 is coupled. The terminal end of the glucose sensor 21 is a spotting portion 21a to which the blood or the control solution 20 is spotted. When a user performs the test for the normality of the measuring apparatus 22 based on the use of the control solution 20, then the user holds, by hand, the measuring apparatus 22 to which the glucose sensor 21 is coupled, and the user brings the spotting portion 21a into contact with the control solution 20 stored in the recess 14 to perform the spotting. The glucose sensor 21 has a flow passage for the spotted blood or the control solution 20, and the glucose sensor 21 has an electrode and a reagent provided in the flow passage.

The measuring apparatus 22 applies a predetermined voltage to the electrode provided for the glucose sensor 21 described above. The measuring apparatus 22 detects the current (referred to as "response current") generated by the electrochemical reaction of the blood or the control solution 20 caused by the application of the voltage. The measuring apparatus 22 calculates the value obtained by converting the response current into the glucose concentration, and the value is displayed on a display 23.

The control solution 20 is a glucose-containing solution in which the glucose concentration is adjusted so that a predetermined glucose concentration is displayed on the display 23 as a result of the measurement with the measuring apparatus 22. However, the component of the control solution is appropriately changed depending on the body fluid component as the measurement object. The user can recognize that the measuring apparatus 22 is normal according to the fact that the measurement result (glucose concentration) of the control solution 20 displayed on the display 23 indicates the predetermined value. On the contrary, if the measurement result is any value other than the predetermined value, the user can judge that at least one of the measuring apparatus 22 and the glucose sensor 21 may be possibly abnormal.

According to the first embodiment, the back surface of the accommodating container 10 is directed upwardly, and the second member 12 (storage portion 17) is folded back to the first member 11 (accommodating portion 13) by using the groove 18. Thus, the desired amount of the control solution 20 can be stored in the recess 14, and the spotting operation can be performed. In this case, it is unnecessary to perform such operations that a screw cap of a bottle accommodated with the control solution is detached and/or a predetermined amount of the control solution is dripped from the bottle to an appropriate place. Therefore, the spotting operation is easily performed. Further, it is easy to avoid the adhesion of the control solution to hands.

Further, the control solution 20, which is in an amount used for the test to be performed once, is accommodated in the accommodating container 10, which is disposable. Thus, any complicated operation is dissolved, which would be otherwise performed, for example, such that the screw cap is attached to the bottle again and/or the bottle is kept. Further, it is possible to suppress the cost of the accommodating container 10 owing to the decrease in the amount of accommodation of the control solution 20. It is possible to properly correspond to the demand for the test at home owing to the adoption of the accommodating container 10 as described above.

Figure 5:
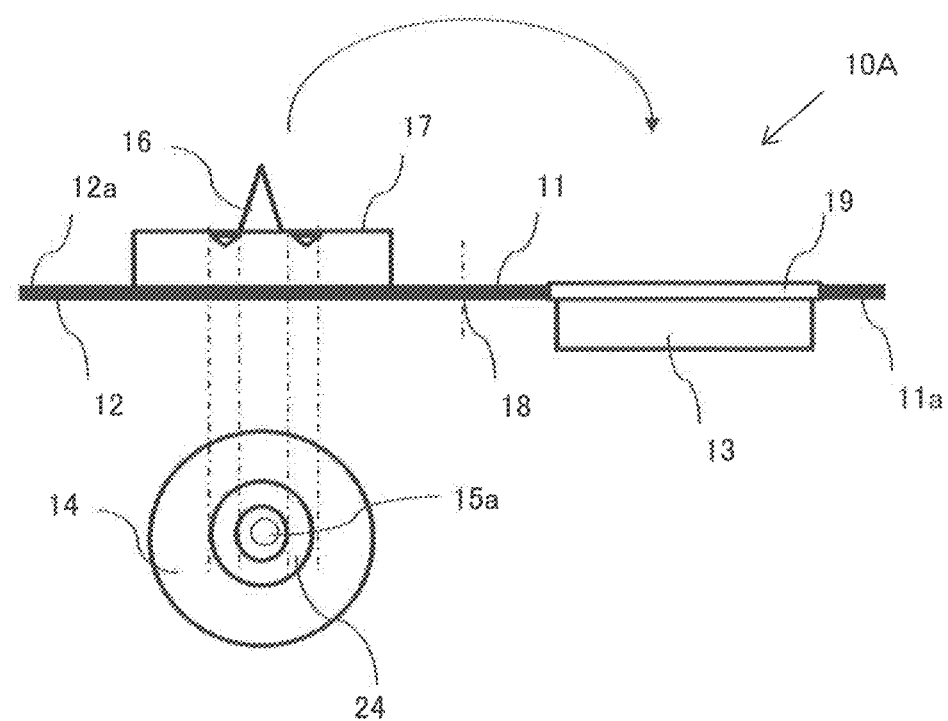
FIG. 5 schematically illustrates a modified embodiment of the accommodating container according to the first embodiment.

FIG. 5 schematically illustrates a modified embodiment (an accommodating container 10A) of the accommodating container 10 according to the first embodiment. In the case of the accommodating container 10A, as illustrated in FIG. 5, an annular protrusion 24, which surrounds the periphery of an opening 15a, is formed at the bottom of a recess 14 of a second member 12 (an storage portion 17). The annular protrusion 24 functions as the limiting portion for limiting the range of diffusion of the control solution 20 discharged from the opening 15a into the recess 14. The annular protrusion 24 makes it possible to allow the control solution 20 to have a depth suitable for the spotting, even if the control solution 20, which is discharged from the recess 13a into the recess 14, is in a small amount.

Second Embodiment

A second embodiment will be explained below. The structure or arrangement of the second embodiment includes features common to those of the first embodiment. Therefore, different features will be principally explained, and common features will be omitted from the explanation.

Figure 6:
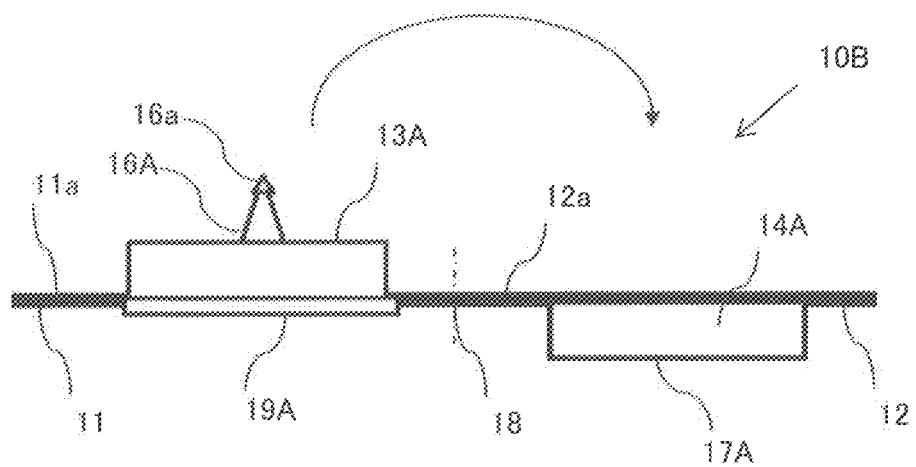
FIG. 6 schematically illustrates a structure of an accommodating container according to a second embodiment.

FIG. 6 schematically illustrates a structure of an accommodating container 10B according to the second embodiment. In the case of the accommodating container 10B, a first member 11 has an accommodating portion 13A. The interior of the accommodating portion 13A is hollow. The interior is open at a downward position as viewed in FIG. 6 to form a recess. The interior (recess) of the accommodating portion 13A is filled with the control solution, which is hermetically closed by a lid 19A. Any lid, which is the same as or equivalent to the lid 19 explained in the first embodiment, can be applied to the lid 19A.

Further, a projection portion 16A, which projects from a central portion of the bottom surface (upper surface as illustrated in FIG. 6) of the accommodating portion 13A, is provided for the accommodating portion 13A. The projection portion 16A has a through-hole which is communicated with the interior of the accommodating portion 13A. An opening is provided at the forward end of the projection portion 16A. A cap 16a is provided at the opening, and the interior of the accommodating portion 13A is hermetically closed. Any member other than the cap 16a may be used to close the opening.

A second member 12 is provided with a storage portion 17A having a recess 14A which is open upwardly as viewed in FIG. 6. The lower edge of the accommodating portion 13A is coupled to a flange 11a, and the upper edge of the storage portion 17A is coupled to a flange 12a. The flange 11a and the flange 12a function as the coupling portions for foldably coupling the accommodating portion 13A to the storage portion 17A. A groove 18 (cut or notch) is formed between the first member 11 and the second member 12 in the same manner as the first embodiment, which is easily foldable back in the fold-back direction illustrated by the arrow in FIG. 6. A perforation or a crease may be provided in place of the groove 18 in the same manner as the first embodiment.

When the accommodating container 10B is used (when the measuring apparatus 22 is tested), the accommodating portion 13A is folded back to the storage portion 17A. The cap 16a is detached in a state in which the forward end of the projection portion 16A is opposed to the recess 14A of the storage portion 17A. The lid 19A is pushed, for example, by finger. The lid 19A has the flexibility, and the lid 19A is recessed to the inside of the recess 13a. In this situation, the control solution, which is accommodated in the accommodating portion 13A, is extruded from the opening disposed at the forward end of the projection portion 16A. The control solution falls into the recess 14A, and the control solution is stored in the recess 14A.

In this way, in the second embodiment, the accommodating portion 13A is formed foldably back with respect to the storage portion 17A. The accommodating portion 13A has the opening of the projection portion 16A as the discharge port for the control solution. Upon the folding back, the opening is positioned over the storage portion 17A.

A user spots the control solution stored at the bottom of the recess 14A onto the glucose sensor 21. The surface, which forms the recess 14A, may be a spherical surface. Further, a limiting portion, which limits the range of diffusion of the control solution, can be provided at the bottom of the recess 14A. For example, it is also appropriate to provide the following arrangement. That is, a hydrophilic area is provided. A peripheral area, which has the hydrophilicity lower than that of the hydrophilic area, is provided around the hydrophilic area. The control solution, which comes from the accommodating portion 13A, is dripped to the hydrophilic area so that the diffusion is limited from the hydrophilic area to the peripheral area. Thus, a bulged shape (for example, a hemispherical shape) of the control solution is formed. Alternatively, the surface, which forms the recess 14A, may be formed to have the hydrophobicity.

Figure 7:
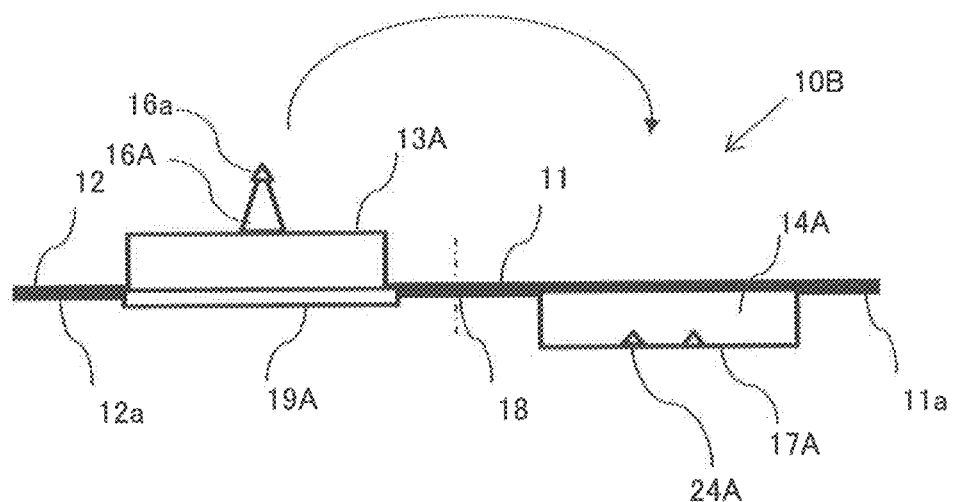
FIG. 7 schematically illustrates a first modified embodiment of the accommodating container according to the second embodiment.
Figure 8:
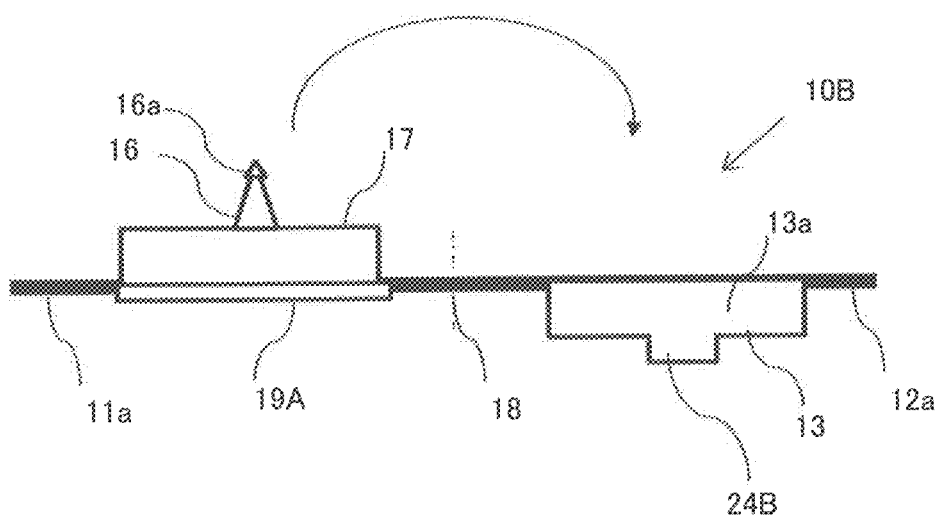
FIG. 8 schematically illustrates a second modified embodiment of the accommodating container according to the second embodiment.

Alternatively, as illustrated in a first modified embodiment in FIG. 7, an annular protrusion 24A, which serves as the limiting portion, may be provided at the bottom of the recess 14A, and the control solution may be dripped into the annular protrusion 24A from the accommodating portion 13A. Further alternatively, as illustrated in a second modified embodiment in FIG. 8, a depression 24B, which serves as the limiting portion, may be provided at the bottom of the recess 14A, and the control solution may be dripped into the depression 24B from the accommodating portion 13A. The same or equivalent effects as those of the first embodiment can be also obtained with the accommodating container 10B of the second embodiment. The structures and the arrangements explained in the embodiments can be appropriately combined with each other.

According to the above-described embodiments, it is possible to provide a liquid accommodating container which makes it easy to handle a liquid for testing a measuring apparatus.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiments of the present invention have been described in detail, it should be understood that the various changes, substitutions, and alterations could be made hereto without departing from the spirit and scope of the invention.

What is claimed is:

1. A liquid accommodating container, comprising:
 a member including:
  a first region including an accommodating reservoir, the accommodating reservoir being configured to accommodate, in a hermetically closed state, a liquid for testing a measuring apparatus; and
  a second region spaced apart from the first region, the second region including a storage reservoir, the storage reservoir being configured to store the liquid; and
 a flange disposed on the member, the flange being configured to couple the accommodating reservoir and the storage reservoir when the accommodating reservoir and the storage reservoir are folded together,
 wherein at least one of a groove, a perforation, and a crease is formed on the flange at a position between the first region and the second region,
 the storage reservoir is formed to be folded towards the accommodating reservoir in a folding direction,
 the storage reservoir includes a projection configured to perforate the accommodating reservoir when the storage reservoir is folded towards the accommodating reservoir, and
 the projection includes a flow passage for the liquid which makes communication between the accommodating reservoir and the storage reservoir when the storage reservoir is folded towards the accommodating reservoir.

2. The liquid accommodating container according to claim 1, wherein:
 the storage reservoir has a recess which is recessed in the folding direction in which the storage reservoir is folded towards the accommodating reservoir; and
 the projection has one end which protrudes in the folding direction and which is open in the recess and an other end which is to be inserted into the liquid contained in the accommodating reservoir when the storage reservoir is folded towards the accommodating reservoir.

3. The liquid accommodating container according to claim 1, wherein the storage reservoir includes a limiting portion which limits a range of diffusion of the liquid which passes through the flow passage and which is discharged into the storage reservoir.

4. The liquid accommodating container according to claim 2, wherein a first area, which is provided around one end of a through-hole of the projection, has hydrophobicity which is lower than hydrophobicity of a second area which surrounds the first area.

5. The liquid accommodating container according to claim 3, wherein the limiting portion has an annular protrusion which is provided around one end of a through-hole of the projection.

6. The liquid accommodating container according to claim 1, wherein:
 the accommodating reservoir is formed to be folded towards to the storage reservoir; and
 the accommodating reservoir has a discharge port for the liquid which is positioned over the storage reservoir when the accommodating reservoir is folded towards the storage reservoir.

7. The liquid accommodating container according to claim 6, wherein the storage reservoir includes a limiting portion which limits a range of diffusion of the liquid discharged from the discharge port.

8. The liquid accommodating container according to claim 1, wherein the liquid is a control solution which is to be used for a test for the measuring apparatus for measuring a glucose concentration in a sample.

* * * * *